(12) United States Patent
Tumialan

(10) Patent No.: US 11,523,913 B1
(45) Date of Patent: Dec. 13, 2022

(54) SPINAL PLATE SYSTEM AND RELATED METHODS

(71) Applicant: Luis M. Tumialan, Paradise Valley, AZ (US)

(72) Inventor: Luis M. Tumialan, Paradise Valley, AZ (US)

( * ) Notice: Subject to any disclaimer, the term of this patent is extended or adjusted under 35 U.S.C. 154(b) by 205 days.

(21) Appl. No.: 16/940,834

(22) Filed: Jul. 28, 2020

Related U.S. Application Data

(63) Continuation of application No. 15/655,720, filed on Jul. 20, 2017, now Pat. No. 10,751,191, which is a continuation of application No. 14/493,183, filed on Sep. 22, 2014, now Pat. No. 10,039,583, which is a continuation of application No. 13/525,313, filed on Jun. 16, 2012, now Pat. No. 8,840,667.

(60) Provisional application No. 61/511,639, filed on Jul. 26, 2011, provisional application No. 61/497,528, filed on Jun. 16, 2011.

(51) Int. Cl.
*A61F 2/44* (2006.01)
*A61B 17/80* (2006.01)
*A61B 17/70* (2006.01)

(52) U.S. Cl.
CPC ............ *A61F 2/44* (2013.01); *A61B 17/7059* (2013.01); *A61B 17/8061* (2013.01)

(58) Field of Classification Search
CPC . A61B 17/80; A61B 17/8033; A61B 17/8061; A61B 17/808; A61B 17/8095; A61F 2/44; A61F 2/442; A61F 2002/4435; A61F 2002/444; A61F 2/4455
USPC ....... 623/17.11–17.16; 606/70, 71, 280–299, 606/90, 96, 87
See application file for complete search history.

(56) References Cited

U.S. PATENT DOCUMENTS

| 7,172,627 | B2 | 2/2007 | Fiere et al. |
| 7,914,562 | B2 | 3/2011 | Zielinski |
| 8,052,729 | B2 | 11/2011 | Dube |
| 2001/0020185 | A1 | 9/2001 | Ray |
| 2002/0091392 | A1 | 7/2002 | Michelson |
| 2003/0135217 | A1 | 7/2003 | Butterman et al. |
| 2004/0092929 | A1 | 5/2004 | Zindrick |

(Continued)

OTHER PUBLICATIONS

Brochure by Medtronic Sofamore Danek titled "VENTURE Anterior Cervical Plate System Surgical Technique". Published at least as early as Jun. 16, 2011.

*Primary Examiner* — Eduardo C Robert
*Assistant Examiner* — Christina Negrellirodriguez
(74) *Attorney, Agent, or Firm* — Adam R. Stephenson, Ltd.

(57) ABSTRACT

Implementations of devices for use in cervical spinal operations. Implementations may include a template including a central hole therethrough and two or more screw holes therethrough. The central hole may be configured to be inserted over a handle of a trial. The template may be configured to place a first of the two or more screw holes over a rostral vertebra and to place a second of the two or more screw holes over a caudal vertebra. Implementations may also include a template including a central hole therethrough and two or more screw holes therethrough. The central hole may be configured to couple over an inserter. The template may be configured to place a first of the two or more screw holes over a rostral vertebra and to place a second of the two or more screw holes over a caudal vertebra.

16 Claims, 14 Drawing Sheets

(56) References Cited

U.S. PATENT DOCUMENTS

| | | | |
|---|---|---|---|
| 2005/0159813 A1* | 7/2005 | Molz | A61F 2/4611 |
| | | | 623/17.11 |
| 2006/0229727 A1* | 10/2006 | Foley | A61F 2/447 |
| | | | 606/90 |
| 2009/0182430 A1 | 7/2009 | Tyber et al. | |
| 2010/0106196 A1 | 4/2010 | Erickson et al. | |
| 2010/0152781 A1 | 4/2010 | Nehls | |
| 2010/0280620 A1 | 11/2010 | Reichen et al. | |

\* cited by examiner

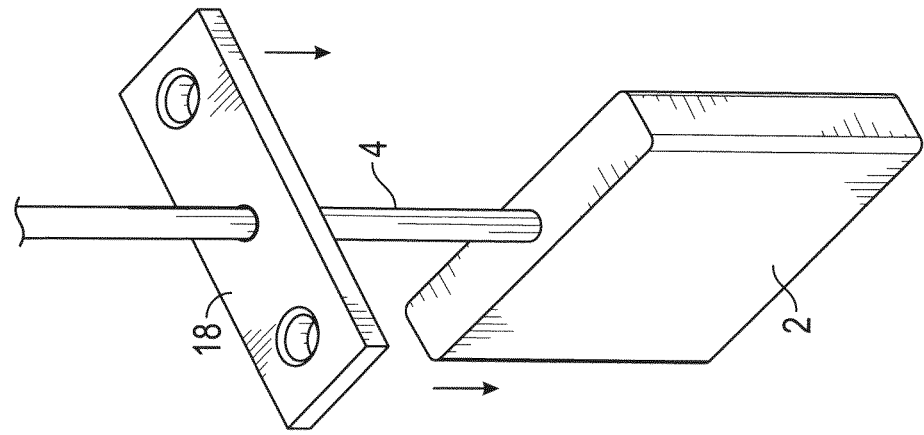
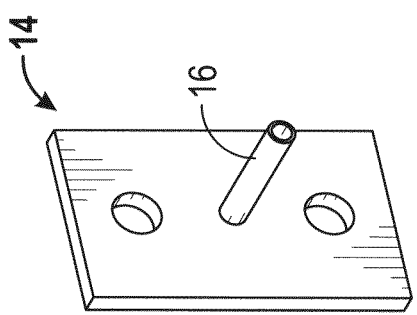
FIG. 1
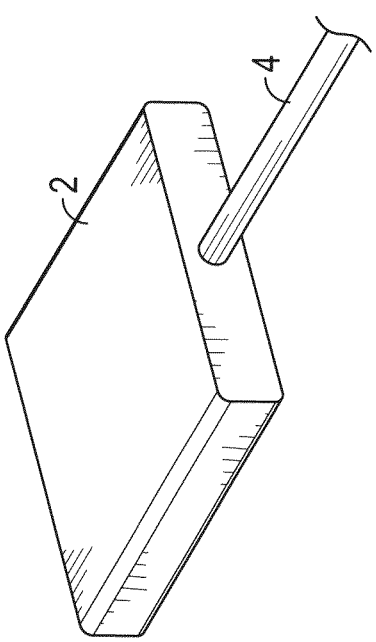
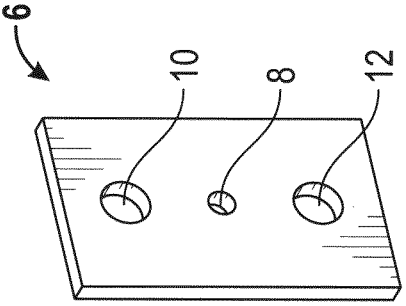

SPINAL PLATE SYSTEM AND RELATED METHODS

CROSS REFERENCE TO RELATED APPLICATIONS

This application is a continuation application of U.S. patent application Ser. No. 15/655,720, titled "Spinal Plate System and Related Methods," to Luis M. Tumialán, filed Jul. 20, 2017, now pending, which is a continuation application of U.S. patent application Ser. No. 14/493,183, titled "Spinal Plate System and Related Methods," to Luis M. Tumialán, filed Sep. 22, 2014 and issued on Aug. 7, 2018 as U.S. Pat. No. 10,039,583, which is a continuation application of U.S. patent application Ser. No. 13/525,313, titled "Spinal Plate System and Related Methods," to Luis M. Tumialán, filed Jun. 16, 2012 and issued on Sep. 23, 2014 as U.S. Pat. No. 8,840,667, which application claims the benefit of the filing date of U.S. Provisional Patent Application 61/497,528, entitled "Cervical Plate System and Related Methods" to Luis M. Tumialán which was filed on Jun. 16, 2011, and also claims the benefit of the filing date of U.S. Provisional Patent Application 61/511,639 entitled "Cervical Plate System and Related Methods" to Luis M. Tumialán which was filed on Jul. 26, 2011, the disclosures of which are each hereby incorporated entirely herein by reference.

BACKGROUND

1. Technical Field

Aspects of this document relate generally to spinal plate systems, such as those used in spinal vertebral fusion operations and procedures.

2. Background Art

Cervical spinal vertebral fusion surgeries generally involve the steps of surgical exposure of two or more vertebrae, removal of the disc between the vertebrae (discectomy and decompression), placement of an interbody graft between the vertebrae to maintain a desired spacing between the vertebrae (the size of the interbody graft being determined using a metal spacer or trial inserted between the vertebrae), and the screwing of a metal plate to the two or more vertebrae to hold them and the graft in place while physical fusion of the bone of the vertebrae takes place.

SUMMARY

Implementations of cervical spinal surgical systems may utilize implementations of devices for use in cervical spinal surgeries. Implementations may include a template including a central hole therethrough and two or more screw holes therethrough. The central hole may be configured to be inserted over a handle of a trial. The template may be configured to place a first of the two or more screw holes over a rostral vertebra and to place a second of the two or more screw holes over a caudal vertebra.

Implementations of devices for use in cervical spinal operations may include one, all, or any of the following:

The two or more screw holes may be centering holes configured to permit a user to drill two or more centering holes into one or more vertebrae for two or more centering pins for a plate.

The two or more screw holes may be pilot screw holes configured to permit a user to drill two or more pilot holes into one or more vertebrae for two or more plate screws.

The template may include only two pilot screw holes and a first of the only two pilot screw holes may be located on a first side of a midline and a second of the only two pilot screw holes may be located along a second side of the midline and the only two pilot screw holes may also be located along a diagonal line extending through each of the only two pilot screw holes and the central hole of the template.

The template may include only four pilot screw holes each of which are configured to align with the position of a corresponding one of four plate screw holes comprised in a plate.

The template may include a sleeve coupled to the template at the central hole where the sleeve is oriented substantially perpendicularly to the template and extends around the central hole.

A plate may be included which may include two or more centering slots therethrough configured to permit the plate to move rostrally and caudally when the plate is placed over the or more centering screws screwed into the one or more vertebrae.

The template may include a first portion and a second portion where the first portion includes the two or more screw holes therethrough and a centering hole and the second portion includes a centering hole and a second center hole.

Implementations of cervical spinal surgical systems may utilize implementations of devices for use in cervical spinal operations. Implementations may include a template including a central hole therethrough and two or more screw holes therethrough. The central hole may be configured to couple over an inserter. The template may be configured to place a first of the two or more screw holes over a rostral vertebra and to place a second of the two or more screw holes over a caudal vertebra.

Implementations of devices for use in cervical spinal operations may include one, all, or any of the following:

The two or more screw holes may be centering holes configured to permit a user to drill two or more centering holes into one or more vertebrae for two or more centering pins for a plate.

The two or more screw holes may be pilot screw holes configured to permit a user to drill two or more pilot screw holes into one or more vertebrae for two or more plate screws.

The template may include only two pilot screw holes and a first of the only two pilot screw holes may be located on a first side of a midline and a second of the only two pilot screw holes may be located on a second side of the midline and the only two pilot screw holes may be also located along a diagonal extending through each of the only two pilot screw holes and the central hole of the template.

The template may include only four pilot screw holes, each of which are configured to align with the position of a corresponding one of four plate screw holes included in a plate.

A coupling member may be included configured to couple to the inserted coupled to a graft and configured to secure a plate to the graft through coupling to the inserter.

The coupling member may further include a center piece coupled to two side blocks through a dovetail joint in each of the two side blocks.

The template may include a first portion and a second portion where the first portion includes the two or more screw holes therethrough and a centering hole and the second portion includes a centering hole and a second center hole.

The template may further include a sleeve coupled to the template at the central hole where the sleeve is oriented substantially perpendicularly to the template and extends around the central hole.

The template may include two prongs configured to engage with template openings in the graft and the inserter may include a flange at an end of the inserter opposing the graft where the flange is configured to slidably engage with an end of the sleeve as the inserter is coupled with the graft and to secure the template to the graft through the flange when the inserter is fully coupled with the graft.

Implementations of cervical spinal surgical systems may utilize implementations of a device for use in a cervical spinal operation. Implementations of the device may include a trial having a handle where two opposing edges of the trial each include a slope configured to correspond with a slope of an uncal vertebral joint of a vertebra.

Implementations of devices for use in cervical spinal operations may include one, all, or any of the following:

The trial may be configured to automatically center the handle over the midline position of two vertebrae through the slope included in each of the two opposing edges of the trial.

Implementations of cervical spinal surgical systems may utilize implementations of a device for use in a cervical spinal operation. Implementations of the device may include an interbody graft having two opposing edges which each include a slope configured to correspond with a slope of an uncal vertebral joint of a vertebra.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and:

FIG. 1 is a perspective view of a trial;

FIG. 2A is a perspective view of a first implementation of a template;

FIG. 2B is a perspective view of a second implementation of a template having a sleeve;

FIG. 2C is view of a template implementation being inserted over a handle of a trial;

DESCRIPTION

Figure 3:
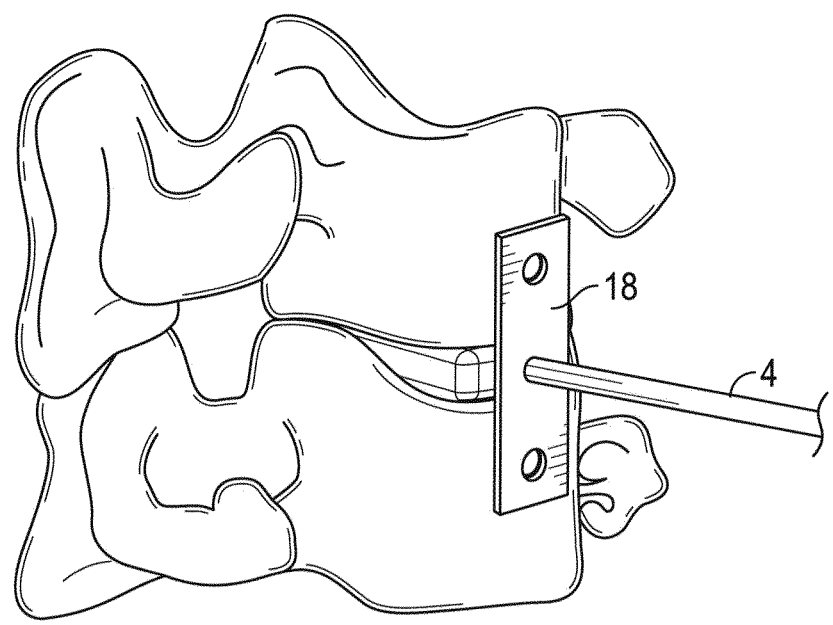
FIG. 3 is a perspective view of a template inserted over the handle of a trial inserted between two vertebrae.

This disclosure, its aspects and implementations, are not limited to the specific components or assembly procedures disclosed herein. Many additional components and assembly procedures known in the art consistent with the intended spinal plate systems and/or assembly procedures for a spinal plate system will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such spinal plate systems and implementing components, consistent with the intended operation.

Implementations of spinal plate systems and related methods may be employed in a wide variety of cervical spinal procedures, including spinal fusion operations and arthroplasty (artificial disc) operations (for simplicity's sake, referred to herein as "spinal surgical systems"). These may include, by non-limiting example, anterior cervical discectomy and fusion (ACDF) and artificial disc placement. In the case of an ACDF operation, such a fusion operation involves the steps of surgical exposure of two or more cervical vertebrae, removal of the disc between two or more cervical vertebrae (discectomy and decompression), placement of an interbody graft between the cervical vertebrae to maintain a desired spacing between the vertebrae (the size of the interbody graft being determined using a metal spacer or trial inserted between the vertebrae), and the screwing of a cervical plate to the two or more cervical vertebrae to hold them and the graft in place while the actual fusion of the bone of the two vertebrae takes place. In many situations, the plate is secured to the anterior aspect of the vertebral body adjacent to the throat with four screws which are located in four holes in the plate. Fluoroscopic imaging is employed during and after the operation and may be taken in the anteroposterior direction (AP, or from front to back, from the throat through the back of the neck) and/or in the lateral direction (from the side of the neck) to determine where the plate and screws are placed relative to the bone of the vertebrae after the plate has been screwed over the bone. Important considerations in determining the success of ACDF surgery may be the orthogonality of the plate, the alignment of the plate with the midline of the vertebrae to which it has been screwed, and whether a plate with the smallest possible length was employed to complete the fusion. It is believed that plates aligned with the midline and which are as short as possible result in the best patient outcomes over time. Oversized plates have been associated with an increased incidence of adjacent segment degeneration, where the vertebral level above the plate degenerates because the presence of the plate acts to erode the disc space. Cervical spinal surgical systems disclosed in this document may simultaneously align the plate over the midline, achieve a plate position orthogonal with the midline while permitting the use of the shortest plate possible in a given surgical procedure.

Cervical spinal surgeries can involve two or more vertebrae. In ACDF and other spinal fusion surgeries, fusions that involve two vertebrae are referred to as single level surgeries, while surgeries that involve three or more vertebrae are referred to as two (or three, etc.) level surgeries. In this document, various implementations of cervical spinal surgical systems that can be utilized in single level surgeries will be discussed, along with implementations that may be utilized in two level surgeries.

In this document, the steps of an ACDF operation are used as an example of a type of spinal fusion surgery that may utilize implementations of cervical spinal surgical systems disclosed herein. However, the use of the ACDF surgical procedure is purely for the exemplary purposes of this disclosure and does not limit the application of the cervical spinal surgical system implementations to only ACDF operations. Those of ordinary skill in the art will readily be able to utilize the principles disclosed herein to apply the various cervical spinal surgical system implementations in many other cervical spinal procedures.

In a single level ACDF surgery, following surgical exposure of the two vertebrae, the midline of the two vertebrae is identified by the surgeon as the point between the uncal vertebral joints, or the midpoint on the width of vertebra between the beginning of the locations where the joints begin to round or slope upward in preparation for engaging with the vertebra above. Identification of the midline can take place either using the longus coli muscles or during decompression using the uncal vertebral joints alone. To create a mark on the midline that can be used throughout the surgery, both the rostral and caudal vertebral bodies may be bovied and tattooed using a marking pen. These marks provide alignment points that are used later in the surgery.

Following discectomy and decompression, the surgeon determines what the proper spacing between the rostral and caudal vertebral bodies should be which determines the size of the interbody graft that should be placed between the vertebrae. The interbody graft works to aid in maintaining the spacing between the two vertebrae during the fusion process following surgery and can facilitate in the process of bone growth between the two vertebrae in some situations, depending upon the materials which make up the graft. Referring to FIG. 1, the spacing is determined using various implementations of trials 2, each of which is a metal plate having a particular thickness with a metal handle 4 attached. Trials come in sets of different sizes, and various sized trials are placed between the two vertebrae until a trial of the desired thickness is identified. Once identified, it is maintained within the two vertebrae and firmly held between the two vertebrae. Because the width of the trial 2 is fairly close to the width of the vertebrae between the slopes of the uncal joints, the handle 4 of the trial generally self-aligns with the midline marks on the two vertebrae.

Because the handle 4 of the trial generally remains self-aligned to the midline during the surgical procedure, implementations of templates like those disclosed herein may utilize the handle of the trial as a reference point in order to drill centering holes or pilot screw holes for a plate.

Referring to FIG. 2A a first implementation of a template 6 is illustrated. As illustrated, the template 6 includes a center hole 8 and two screw holes 10, 12. In this first implementation, the two screw holes 10, 12 are centering holes which are used by the surgeon to drill centering holes (centering screw holes) in the rostral and caudal vertebrae in preparation for the screwing of centering screws into the holes. The use of the centering screws will be discussed later in this document. The center hole 8 is sized to enable the handle 4 of the trial 2 to pass through it, allowing the surgeon to insert the template 6 over the handle 4 of the trial 2 once the trial 2 has been put into position. Once in this position, the template 6 identifies the location of (places) the first centering screw hole 10 over the rostral vertebra and places the second centering screw hole over the caudal vertebra. Simultaneously, the first centering screw hole 10 and second centering screw hole 12 are aligned with the midpoint of both vertebrae since the handle 4 of the trial 2 is self-aligned in the center of the space between the two vertebrae.

Referring to FIG. 2B, a second implementation of a template 14 is illustrated. This template implementation includes a sleeve 16 that is coupled to the template 14 at the center hole and extends outwardly around the center hole substantially perpendicularly relative to the plane formed by the template 14. While the sleeve 16 may be angled substantially perpendicularly, it may also be angled a desired number of degrees rostrally or caudally in order to accommodate a trial with an angled handle or the orientation needed for a specific cervical spinal procedure. The sleeve 16 may serve to further stabilize the template 14 during use while drilling centering screw holes. The sleeve may extend, by non-limiting example, a short distance, most of the length, a majority of the length, or the full length of the handle of the trial in various implementations.

Referring to FIG. 2C, an implementation of a template 18 is illustrated being inserted over the handle 4 of a trial 2 like the one illustrated in FIG. 1. FIG. 3 illustrates the position of the template 18 relative to the rostral and caudal vertebrae and illustrates the centered position of the centering screw holes through their alignment with the handle 4.

Figure 4:
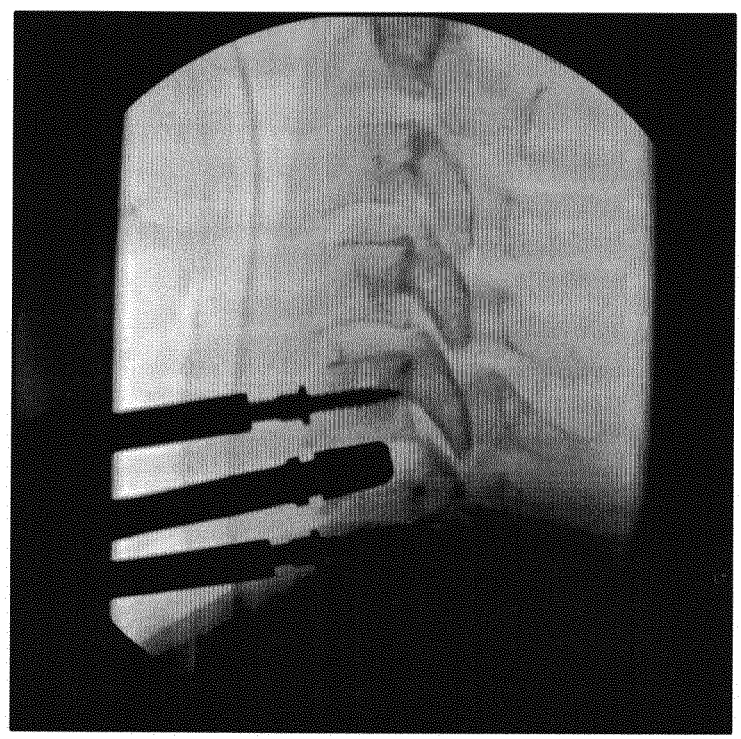
FIG. 4 is an intraoperative lateral fluoroscopic image illustrating a 6 mm lordotic cervical trial in position.

Referring to FIG. 4, an intraoperative lateral fluoroscopic image illustrating a 6 mm lordotic cervical trial inserted between two vertebrae is illustrated. In the image, the trial is located between two centering screws that have been inserted into the rostral and caudal vertebrae located above and below the trial, respectively.

With the template inserted over the trial as illustrated in FIG. 3, the surgeon will inspect the position of the centering screw holes (screw holes) holes on the rostral and caudal vertebrae to determine from the position of the hole in the template if each hole is placed sufficiently far along the vertebra to ensure that adequate bone coverage exists to support a centering pin (centering screw). If the surgeon determines that the coverage is inadequate, the existing template can removed from the handle 4 and a differently sized template (longer or shorter) can be slid over the handle 4. In various implementations of cervical spinal surgical systems the size of the template may correspond directly with the size of the cervical plate that will be used (i.e., dimensions of the template may be the same as the dimensions of the plate, for example, the length of the template and corresponding plate are the same). For the exemplary purposes of this disclosure, the length of the template may range between about 19 mm to about 27 mm in length, though centering pin template sizes that are smaller or larger than these may also be used, depending upon the dimensions of the vertebrae involved and the age and size of the patients. During the process of selecting the proper template size, lateral fluoroscopic imaging may be employed to determine the location of the template that will provide adequate bone coverage for the screws and confirm and verify that the proper length has been selected. The use of a metal template means that the template is visible using lateral fluoroscopic imaging. Further, since the template 18 is already centered over the midline through being coupled to the trial handle 4, the needed length of the cervical plate may be determined without the need to separately use AP fluoroscopic imaging to verify the plate length and/or position relative to the midline.

Figure 5:
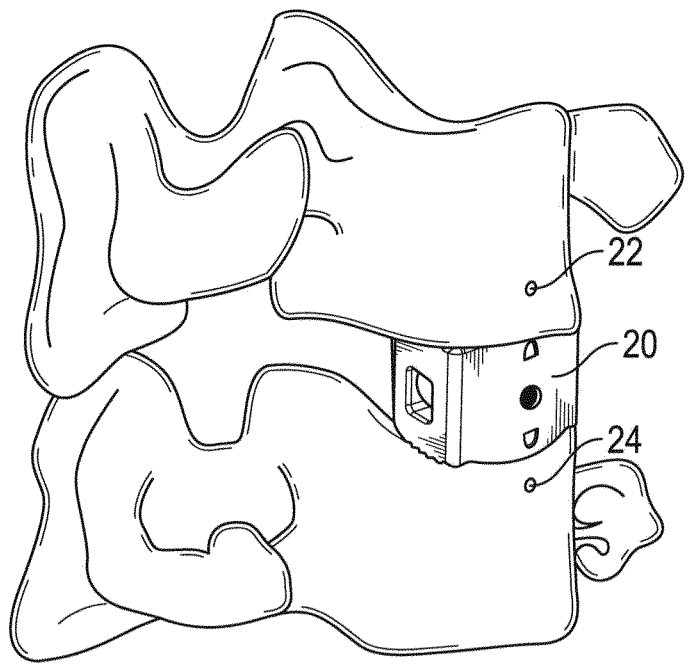
FIG. 5 is a perspective view of a graft inserted between two vertebrae illustrating the position of two centering holes.

Once a desired template 18 has been determined, the centering holes are drilled using the centering screw holes in the template 18, and the template 18 and trial 4 are removed. Referring to FIG. 5, an interbody graft 20 is then placed between the vertebrae. Implementations of interbody grafts that may be used in implementations of cervical spinal surgical systems disclosed in this document may include any conventional graft type including those made of polyetheretherketone (PEEK), cortical cancellous grafts, other material types, and those that include autograft or allograft materials within their interior to facilitate the fusion process. Due to the width of many conventional grafts, following surgery, the graft generally naturally automatically centers itself with respect to the midline and can be used in imaging to establish a reference point to see how centered the plate is following surgery. Once the interbody graft is placed, centering pins are screwed into the already drilled centering holes 22, 24. FIG. 5 illustrates the placement of the graft 20 and the drilled centering holes 22, 24 after the trial and centering pin template have been removed. In various implementations, the centering pins need to extend about 14 mm to about 15 mm into the bone to properly hold the plate in place and may extend about 6 mm above the bone.

Figure 6A:
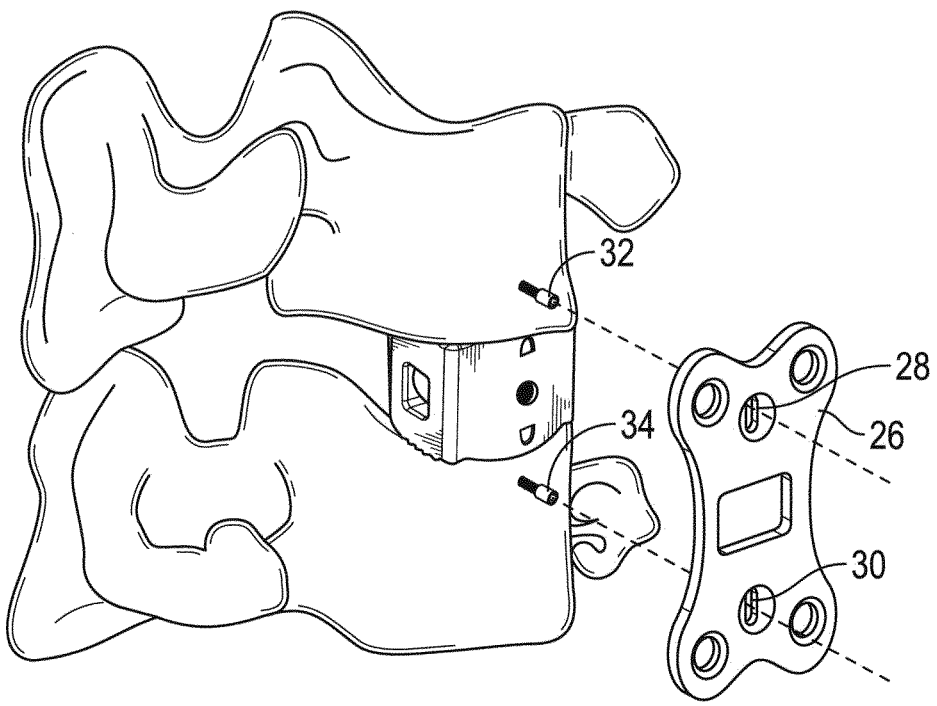
FIG. 6A is an exploded view of a plate adjacent to two centering screws inserted into two vertebrae.
Figure 6B:
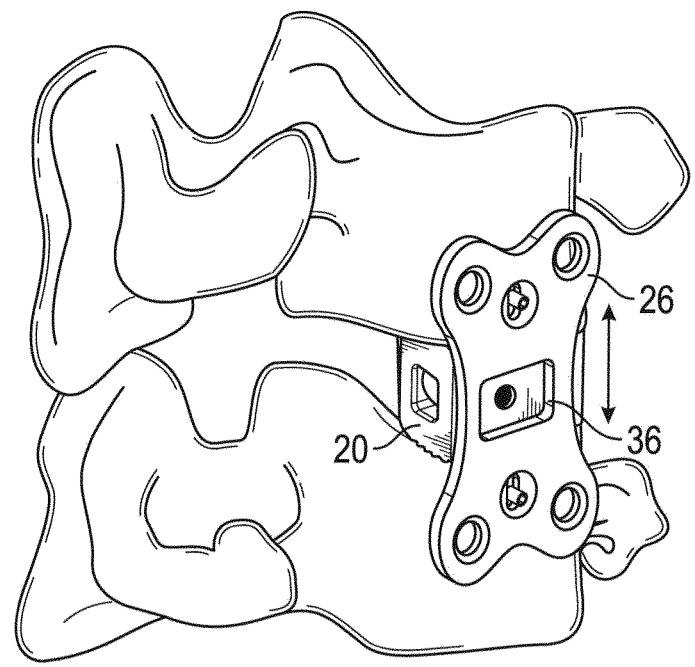
FIG. 6B is a perspective view of a plate coupled over the two centering screws through two centering slots.

Some conventionally available cervical plate systems are include openings for centering pins, such as the anterior cervical plate system marketed under the tradename VENTURE™ by Medtronic Sofamor Danek USA, Inc. of Memphis Tenn. Depending upon the degree of parallelism between the two centering pins, the distance between the two centering pins may vary too much in some applications for a conventional cervical plate having openings for centering pins to be inserted over the centering pins. Referring to FIG. 6A, an implementation of a plate 26 that includes centering slots 28, 30 that provide flexibility to handle distance variations between the centering screws 32, 34. The presence of the centering slots 28, 30 also may provide the ability to allow for rostral and caudal adjustment of the position of the cervical plate while the plate 26 is placed over the centering screws 32, 34. During surgery, the rostral or caudal position of the plate on the vertebrae may need to be adjusted to ensure that the plate screw holes that secure the plate 26 to the vertebrae are drilled into the vertebrae with sufficient bone coverage and/or support. Because the tolerance of the centering slots to the centering pins may be designed to be very small in the left and right directions, the plate 26 can be moved rostrally and caudally to a desired position without moving in the left or right direction and thereby losing the alignment of the plate 26 over the midline. The position of a plate 26 implementation over the vertebrae is illustrated in FIG. 6B, showing the ability of the plate 26 to move rostrally and caudally. The plate 26 also contains a window 36 at the location where the plate 26 meets the graft 20.

Once the plate 26 is in the desired position, the pilot screw holes for the four screws that hold the plate 26 to the two vertebrae are drilled. Generally this is done using fixed angle drill guides which allow the surgeon to place each screw in its own individually angled hole within the vertebrae. Self-tapping screws may also be utilized in specific implementations. Relevant disclosure regarding the drilling equipment and techniques that may be used to perform the pilot hole drilling may be found in materials found in Appendix A to U.S. Provisional Patent Application 61/497,528, entitled "Cervical Plate System and Related Methods" to Luis Tumialán which was filed on Jun. 16, 2011 (the '528 provisional) which was previously incorporated by reference.

In other system implementations, centering pins may not be utilized. In these implementations, after the template 18 is used to drill the centering holes 22, 24, the plate may be placed directly over the centering holes 22, 24 and plate holding pins may be screwed through plate holding pin holes in the plate. The plate holding pins then physically hold the plate in position over the midline and in position while the pilot screw holes for the four plate screws are being drilled. An example of plate holding pins that could be used may be found in the disclosure in Appendix A to the '528 provisional). This technique relies on the ability of the plate holding pins to find the centering holes 22, 24 in order to maintain the position of the plate over the midline. Because this technique does not utilize centering pins, centering pin distance issues are obviated in this approach, but the ability to adjust the position of the plate rostrally and caudally may be reduced significantly, depending upon whether a cervical plate like that illustrated in the '528 provisional or a cervical plate 26 like that illustrated in FIGS. 6A and 6B is utilized.

Figure 7A:
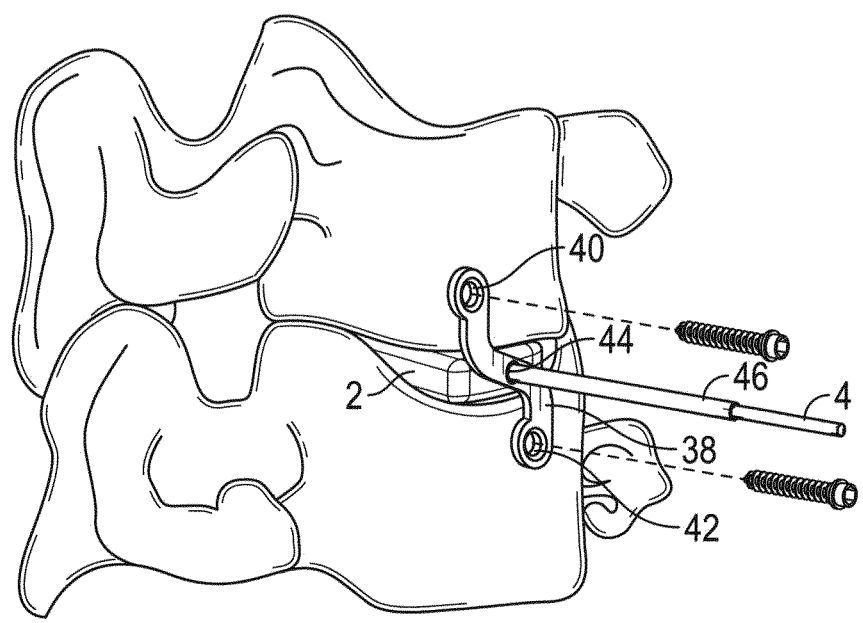
FIG. 7A is a perspective view of a third implementation of a template inserted over a trial handle.

Referring to FIG. 7A, a third implementation of a template 38 is illustrated. As illustrated, the template 38 is sized to indicate where two of the four pilot screw holes should be drilled for a correspondingly sized plate. In this implementation of a template 38, the template 38 directly indicates the position of the pilot screw holes rather than centering holes. In this implementation, the first pilot screw hole 40 is located on a first side of the midline and a second pilot screw hole 42 is located on a second side of the midline. As can be seen by inspection, the first pilot screw hole 40 is diagonally aligned with the second pilot screw hole 42. The central hole 44 is also located along the diagonal line between the first and second pilot screw holes 40, 42 (the central hole 44 is surrounded by sleeve 46 in the template implementation illustrated in FIG. 7A). Because the two pilot screw holes 40, 42 that will be drilled are diagonally aligned, as a matter of geometry, when the plate is screwed into the two pilot screw holes using the plate screws (indicated by the two screws in FIG. 7A, which would be inserted after removal of the template 38 and the placement of a plate over the two pilot screw holes 40, 42), the likelihood that the plate will move from the position over the midline or rostrally or caudally may be greatly minimized while the remaining two pilot screw holes are drilled and the plate screws inserted.

Figure 7B:
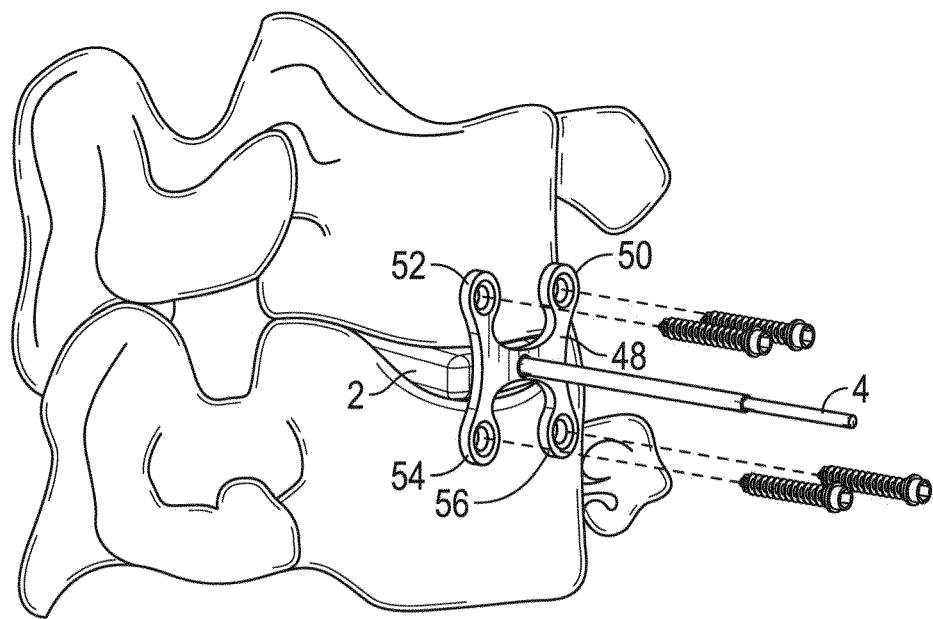
FIG. 7B is a perspective view of a fourth implementation of a template inserted over a trial handle.

Referring to FIG. 7B, a fourth implementation of a template 48 is illustrated. Here, the template 48 indicates the positioning of all four pilot screw holes 50, 52, 54, 56 for a correspondingly sized plate. When such a template 48 has been placed over the handle 4, it likewise indicates the position for the pilot screw holes 50, 52, 54, 56 that may permit the plate to be centered over the midline and help the surgeon as has been described previously, to determine the minimum length of the plate desired. When such a template 48 is in use, the surgeon could drill all four pilot holes 50, 52, 54, 56 using the template 48, remove the template 48 and trial 2 and then directly screw the plate into the four pilot screw holes (as indicated by the four screws in FIG. 7B, which would be inserted after removal of the template 48 and the placement of a plate over the four pilot screw holes 50, 52, 54, 56), relying on the ability of the screws to find/tap the drilled holes and achieve centering of the plate over the midline location set by the template 38. The surgeon could also choose to drill one of the two pairs of the diagonally opposing pilot screw holes (52, 56 or 50, 54) using the template 48 and screw the plate to the vertebrae prior to drilling the remaining pair pilot screw holes. In some implementations, the surgeon could drill the two pilot screw holes on one or the other side of the handle 4 (or for one vertebra or the other) and screw the plate to those pilot screw holes before drilling the remaining pilot screw holes. In implementations where all four pilot screw holes are drilled prior to screwing the plate into the vertebrae, the amount of bleeding from the screw holes in the bone that occurs prior to the screwing on of the cervical plate may become an issue. Accordingly, the surgeon may include the steps of packing the drilled pilot screw holes with gel foam thrombin products or bone wax while the remaining pilot screw holes are being drilled.

In particular implementations, a template that includes only two holes corresponding to the position of pilot screw holes on the cervical plate may include of a pair of holes that are not diagonally aligned (i.e., ones that are on the same side of the midline). Such implementations may be more vulnerable to loss of midline alignment of the cervical plate as the remaining pair of pilot screw holes are drilled when the plate has been screwed to the vertebrae due to rotation of the vertebrae relative to each other during the drilling process.

Figure 8A:
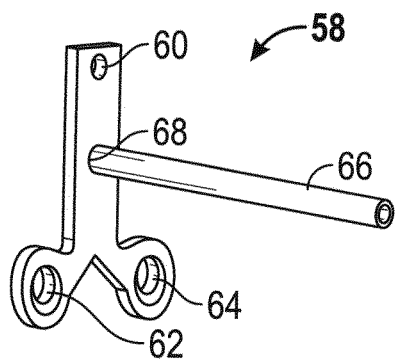
FIG. 8A is a perspective view of a first portion of a fifth implementation of a template.
Figure 8B:
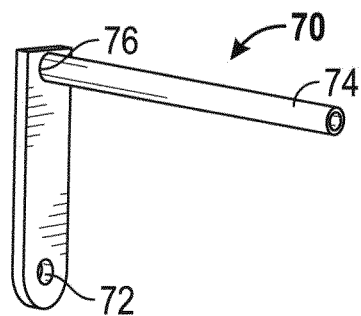
FIG. 8B is a perspective view of a second portion of a fifth implementation of a template.

In situations where two or more level surgeries are taking place, various template implementations may be created to aid in centering the plate over the midline and in determining the total length of the plate as it extends over multiple vertebrae. Referring to FIG. 8A, a first portion 58 of a fifth implementation of a template is illustrated. As illustrated, the first portion contains a centering hole 60 and two pilot screw holes 62, 64 and a sleeve 66 that extends around a center hole 68. Referring to FIG. 8 B, a second portion 70 of the fifth implementation of the template is illustrated. As illustrated, the second portion 70 includes a centering hole 72 and a sleeve 74 that extends around a second center hole 76. The sleeves 66 and 72 are configured to fit over the handles of trials inserted between the various vertebrae being fused during the two or more level procedure.

In implementations of methods of cervical fusion surgery disclosed herein, in a two level surgery, the same principles disclosed above regarding the locating of the midpoint and use of trials to determine the desired spacing are used. The templates utilized, however, are altered to correspond with the different length and number of screw holes of the cervical plate utilized when fusing three or more vertebrae simultaneously. When marking the midline, the surgeon may mark the midline on all of the vertebrae, but the most important marking may be on the middle vertebra (middle body). For example, in a C 4-5, C5-6 ACDF, the marking on the C5 is the most important to determining that the cervical plate aligns to the midpoint of the C4 and C6 vertebrae as well. In some procedures, the first level discectomy and decompression along with the placing of the interbody graft can be completed without utilizing a template. The first level could be either the rostral or caudal to the middle body. Once the discectomy and decompression of the second level has been completed, a trial of the desired width is secured into the second level.

Figure 8C:
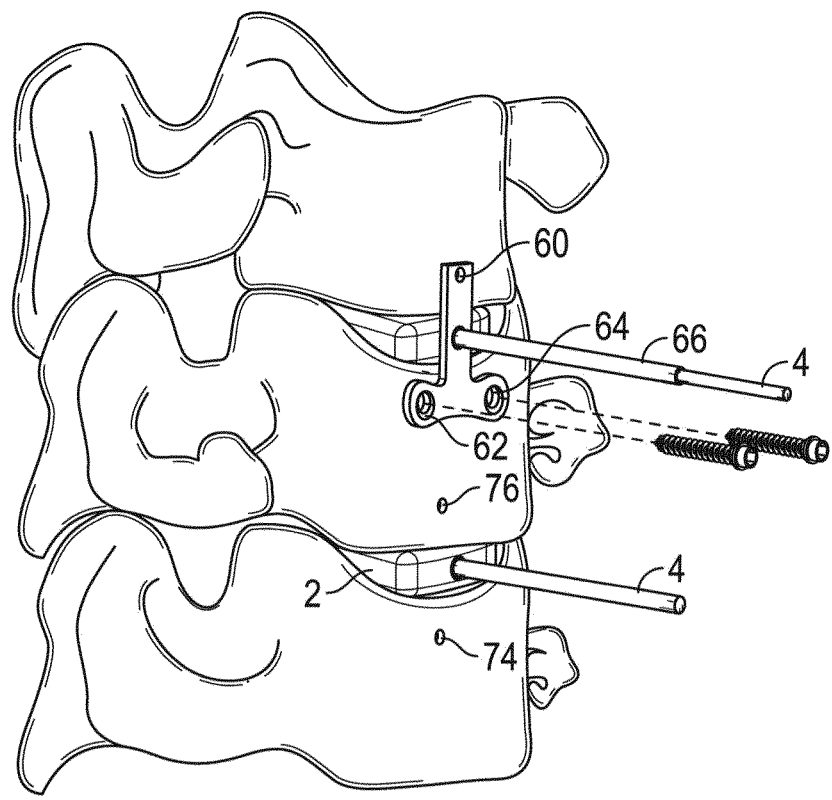
FIG. 8C is a perspective view of a first section of a template inserted over a trial handle after centering holes have been drilled using the second section.

Referring to FIG. 8C, an intermediate position during a two level ACDF surgery is illustrated. In the example illustrated, a trial 2 has placed in the first level, which in this case is the caudal position. In the alternative, as discussed above, the trial 2 could have already been removed and replaced with a graft. The second portion 70 of the template has already been placed over the trial handle 4 and the centering hole 72 has been used to drill centering hole 74 in the most caudal vertebra. Because the second portion 70 is rotatable around the handle 4 through the sleeve 74, the second portion 70 can then be rotated rostrally to allow the surgeon to drill a second centering hole 76 in the vertebra rostral to the most caudal vertebra. The centering hole 76 in the middle vertebra could also have been drilled using the first portion 58 of the template through a similar rotation of the first portion 58 around the handle 4 using the sleeve 66. Currently, the first portion 58 of the template has been inserted over the handle 4 of the trial 2 located between the most rostral vertebra and the vertebra below it. At this point the surgeon is free to drill two pilot screw holes using the pilot screw holes 62, 64 of the first portion 58, or may choose to drill a third centering hole using the centering hole 60. If the surgeon chooses to drill pilot screw holes, the plate can be secured over the midline of the three vertebrae, and the surgeon can then use the centering hole 74, second centering hole 76, and third centering hole (if drilled) and centering pins or plate holding pin to hold the plate in place while the remaining pilot screw holes are drilled prior to final fixation of the plate using plate screws. In the alternative, if the surgeon chose not to drill the pilot screw holes into the middle vertebra, the third centering hole would be drilled and the plate secured either with centering pins or plate holding pins while the pilot screw holes are drilled. Either method permits the plate to be secured to the midline position prior to drilling of any or the rest of the pilot screw holes.

The previous discussion involving the two implementations of plate/centering pin templates has involved the steps involved with aligning the plate with the midline. As an aid in determining the length of the plate, a third portion of the template may be included in particular implementations. Implementations of a third portion of the template may be similar in appearance to the second portion 70 except that they may have a portion that extends rostrally and caudally from around the central hole and has a total length in the rostral and caudal direction that corresponds with the length of various plate implementations. The third portion may also include other dimensions that correspond with the dimensions of various plate implementations. In implementations, the third portion may also include in its superior and inferior ends, centering holes (analogously to the centering hole 72 included in the second portion 70). When placed over the trial handle, the third portion may be used, along with lateral fluoroscopic imaging, to determine the needed length of the plate. In addition, the third template may be used to drill centering holes in the rostral and caudal vertebrae on either side of the middle body.

As can be observed from the previous discussion, the first portion 58, second portion 70, and the third portion of the template could be employed in a number of different sequences and combinations during a two or more level spinal fusion surgery, which can be readily appreciated by those of ordinary skill in the art from the principles disclosed herein. In particular implementations, maintaining simplicity of the structures and techniques involved when performing a two or more level spinal fusion while still securing a midline position for the plate leads to use of a template that permits the surgeon to place two pilot screw holes on each side of the midline on the uppermost vertebra or the lowest vertebra.

A wide variety of sizes for first portion 58, second portion 70, and third portions of the template are possible. For the exemplary purposes of this disclosure, third portion implementations may range from about 32.5 mm to about 42.5 mm in length, first portion implementations may range from about 16 mm to about 21 mm in length, and second portion implementations may range from about 16.5 to about 21.5 mm in length.

The previous discussion discloses the use of various template implementations for drilling of centering holes or pilot screw holes where the template is inserted over the handle of the trial 2. The use of grafts has also been disclosed, and the self-centering behavior of the graft has also been noted. Cadaver allografts are utilized in various spinal fusion surgery methods. In other methods, the graft may be made of polyetheretherketone (PEEK), and may include a center hole located at the midpoint of the side of the graft that faces the cervical plate. The center hole is generally present to allow an inserter to engage with the graft to aid in placing the graft between the two vertebrae. As a result of the natural (or physician assisted) centering of the graft after being placed, the center hole may become substantially aligned with the midpoint of both vertebrae since the graft is likewise aligned.

Figure 9A:
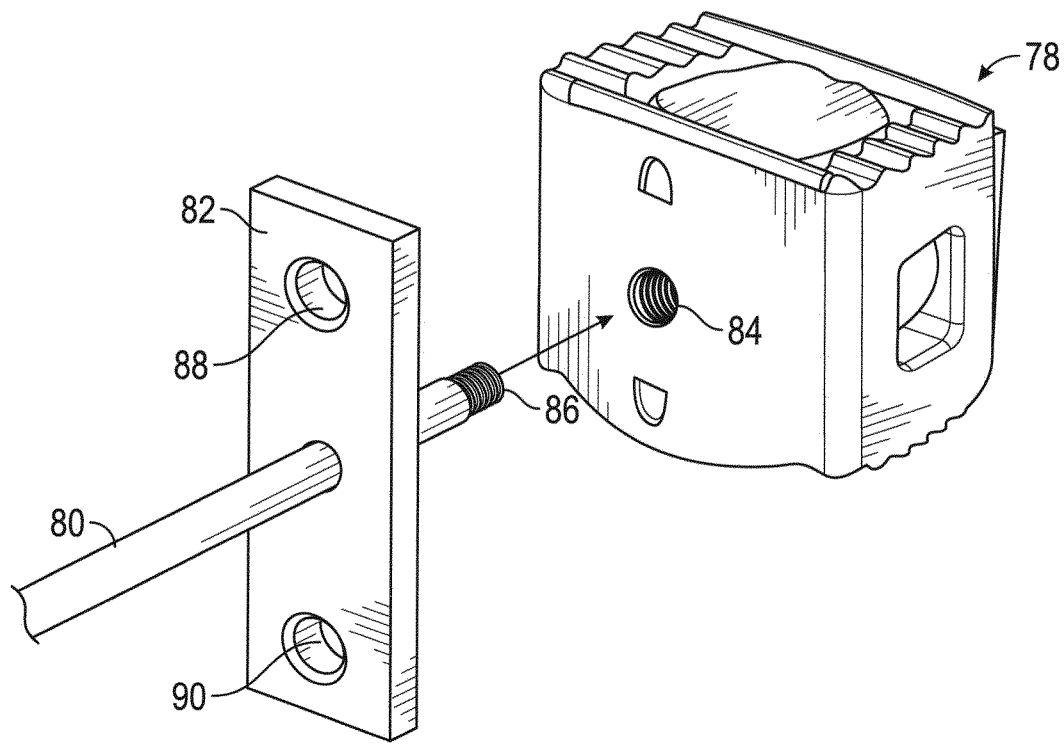
FIG. 9A is an exploded perspective view of a sixth implementation of a template.
Figure 9B:
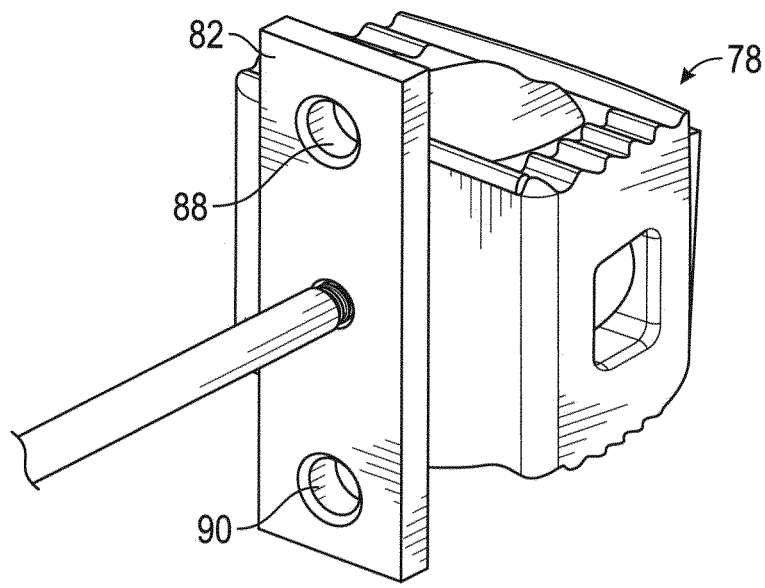
FIG. 9B is a perspective view of the sixth implementation illustrated in FIG. 9A fully coupled to a graft.

Referring to FIG. 9A, an implementation of a graft 78 is illustrated in a exploded view along with an implementation of an inserter 80 and a sixth implementation of a template 82. In various procedure implementations, following placement of the trial, the graft 78 is then inserted using the inserter 80, which screws into the center hole 84 of the graft 78 using threads 86 on the inserter 80. The template 82 can then be placed over the inserter 80, which is still securely fastened to the graft 78 via the threads 84 (see FIG. 9B). In an alternative implementation, the inserter 80 may be removed and replaced with another rod with a similarly threaded end, and the template 82 placed over the rod. Similarly to other template implementations disclosed in this document, the template 82 contains centering holes 88, 90 for use in drilling centering screw holes. Once the centering pin template is in place, the centering screw holes can be drilled, followed by removal of the template and inserter/rod from the center hole of the graft. Plate centering pins or plate holding pins can then be inserted into the bone and used to align and maintain the position of the plate over the midline or secure the plate position over the midline while the pilot screw holes are being drilled.

Figure 10:
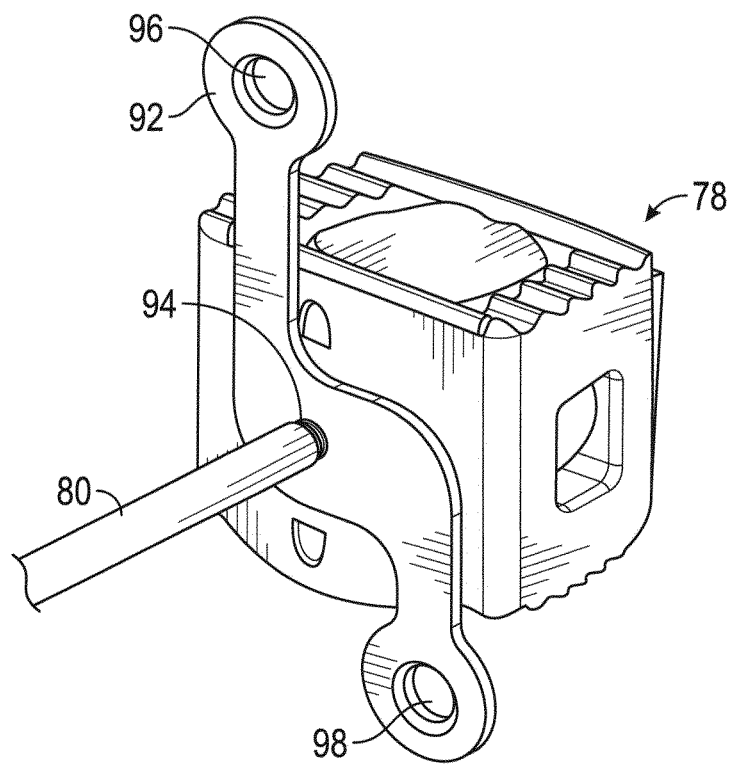
FIG. 10 is a perspective view of a seventh implementation of a template coupled to a graft.

A wide variety of different template shapes, including those already disclosed therein may be utilized in implementations where the template is coupled to the graft rather than to the trial. Referring to FIG. 10, a seventh implementation of a template 92 is illustrated coupled to a graft 78 through inserter 80. As illustrated, the template 92 can be attached to the graft 78 through being placed over the graft 78 once the inserter 80 has been removed and then secured to the graft as the inserter 80 is screwed back into the graft 78, allowing the template 92 to couple with the threads 94 of the inserter 80. The template 92 may also couple over the inserter through a sleeve or central hole as has been described previously. The template 92 illustrated in FIG. 10 functions similarly to the similar template 38 in FIG. 7A and may similarly allow the template 92 to accommodate the fixed angle and/or variable angle drill guides while also ensuring that the pilot screw holes are placed to ensure that the plate is aligned over the midline when secured using the plate screws. While the plate template illustrated in FIGS. 3 and 4 has two openings 96, 98 for two pilot screw holes, other implementations may include additional screw holes, up to the number of pilot screw holes in the plate (for example, the four hole template 48 previously disclosed).

In other implementations of cervical spinal surgical systems, the system may not employ a template, but may operate by directly securing the plate to the graft itself through the inserter or rod. Because implementations of various plates may not contain a window or other opening internal to the plate, particularly those that are relatively short, some plates may be modified to include at least a small circular opening sized to allow the inserter to pass through it located substantially near the plate center to be used in these system and method implementations. Other implementations of plates already contain a window opening in the center region of the plate of varying size and orientation relative to the center of the plate (see window 36 in plate 26 in FIG. 6B for an example).

Figure 11:
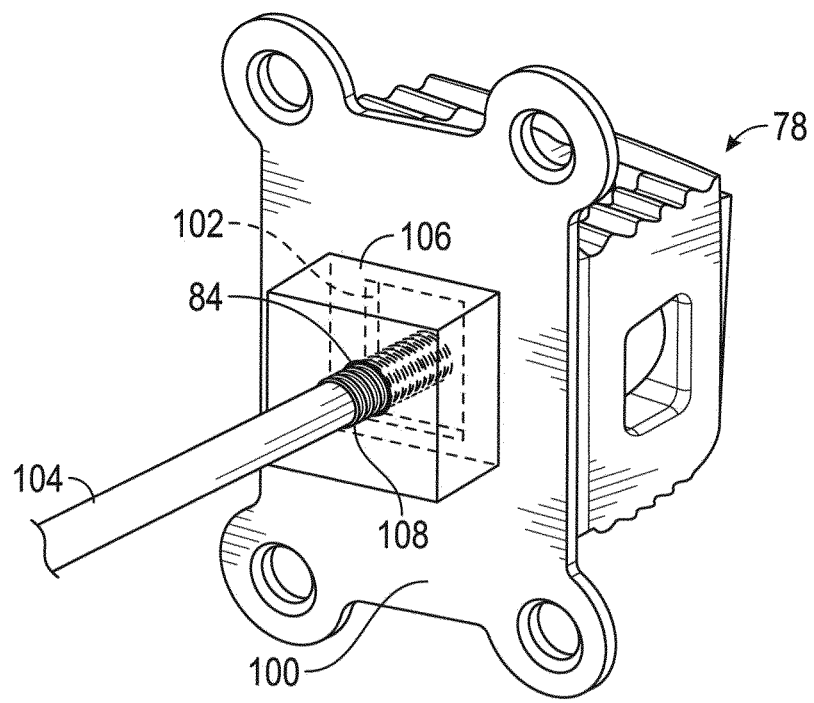
FIG. 11 is a perspective see through view of a plate coupled to a graft through a coupling member.

Referring to FIG. 11, a plate 100 is illustrated coupled to the graft 78. In a first implementation, the coupling takes place by placing the plate 100 over the graft 78, aligning the hole 102 in the plate 100 with the center hole 84 of the graft 78, inserting a rod 104 (which may be an inserter in particular implementations) through the hole 102 in the plate 100 and securing the rod 104 within the center hole 84 of the graft 78. A coupling member 106 (shown here in see through) is then placed over the rod 104 until a threaded portion of an opening in the coupling member 106 engages with exposed threads 108 on the rod 104 that extend above the surface of the plate 100. By rotating the coupling member 106 down the threads 108, the coupling member 106 simultaneously compresses the plate 100 against the graft 78 and secures the coupling member 106 to the graft 78. At this point, the plate 100 is secured against the graft 78 and a variable or fixed angled drill guide may be used to drill the four pilot screw holes prior to the plate being secured to the bone through insertion of the screws.

In a second implementation of the system, the rod 104 remains fixed in the center hole 84 of the graft 78 (or the rod 104 is first screwed into the center hole 84), the plate 100 is inserted over the inserter/rod 104, and the coupling member 106 is placed over the rod 104 and secured over the plate 100 to the graft 78 with the exposed threads 108. In yet another variation, the plate 100 and coupling member 106 are placed over the graft 78 and the openings in each aligned with the center hole 84 of the graft 78. The rod 104 is then inserted into the coupling member 106 and rotated to allow the threads of the rod 104 to pass through the coupling member 106, the plate 100 and into the center hole 84 of the graft 78. The coupling member 106 may then be rotated slightly to ensure that the plate 100 is securely held against the graft 78.

Figure 12:
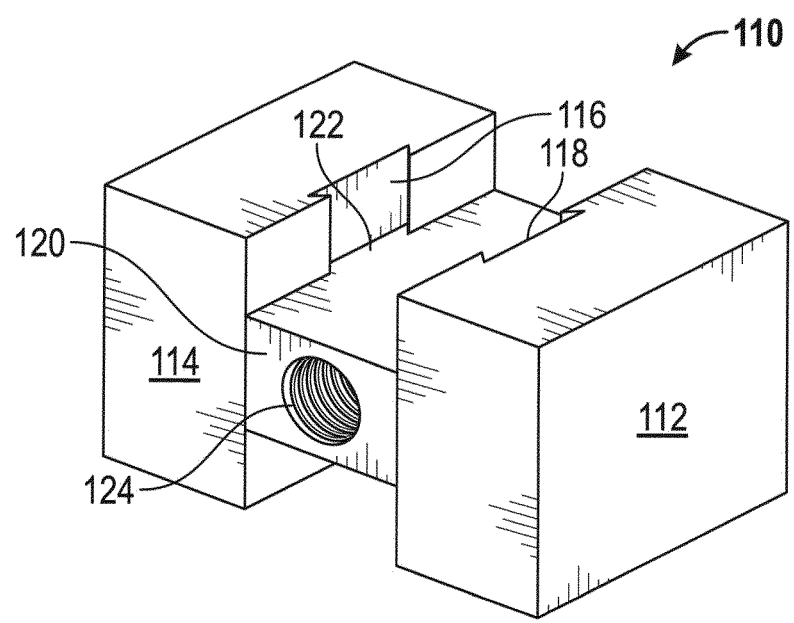
FIG. 12 is a detail perspective view of an implementation of a coupling member.

For implementations of plates that include windows with a rectangular or square dimension, depending upon whether the window is actually located over the plate center or not and depending upon what the desired position of the plate rostrally and caudally is to ensure the best locations for the screws to obtain purchase in the bone, the ability to move the plate rostrally and caudally when coupled to the graft through a coupling member implantation may be advantageous. Referring to FIG. 12, an implementation of a window adaptor 110 that may be used in conjunction with the coupling member 106 previously described or independently is illustrated. As illustrated, the window adaptor 110 includes two side blocks 112, 114 that each have a dovetailed recess 116, 118 in a side of each of the two side blocks 112, 114. The two side blocks 112, 114 are coupled together through a center piece 120 that contains two projections 122 extending from opposing faces of the center piece 120 that each correspond with a respective one of the dovetailed recesses 122, 118 in the two side blocks 112, 114 (or a dovetail joint in each of the two side blocks). The center piece 120 also contains an opening 124 therethrough that is aligned substantially perpendicularly with the dovetailed recesses in the two side blocks (dovetail joints). The opening 124 is adapted to allow the rod 104 to pass through it, and may be threaded.

Figure 13:
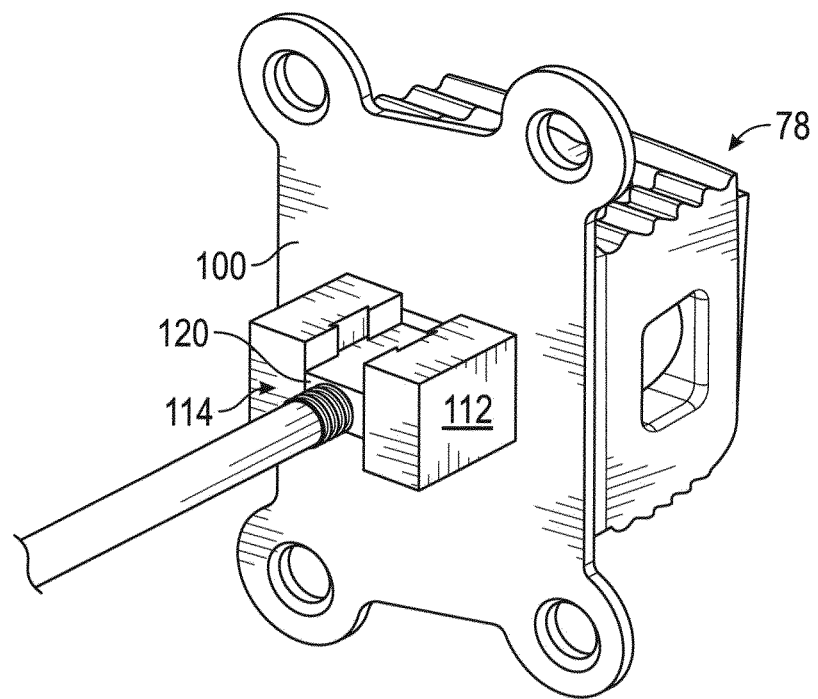
FIG. 13 is a perspective view of the implementation of a coupling member of FIG. 12 coupled over a plate and holding the plate against a graft.

In use, the window adapter 110 is placed over the inserter/rod 104 either before or after the plate 100 has been placed against the graft 78. Depending upon the position of the screw openings in the plate 100 against the rostral and caudal vertebrae, the position of the plate 100 against the vertebrae may be adjusted rostrally and caudally by sliding the two side blocks 112, 114 relative to the center piece 120 using the dovetailed recesses 116, 118 while the two side blocks 112, 114 are engaged with the edges of the window opening (see the implementation illustrated in FIG. 13, where a window adapter 110 is coupled to the plate 100 over the window (not shown as it is under the window adapter 110)). In implementations where the coupling member 106 is used in addition to the window adapter 110, once the plate 100 is in the desired rostral/caudal location, the coupling member 106 may be used to tighten the window adapter 110 against the graft 78 and tighten the plate 100 against the graft 78 to hold it in the desired position. In other implementations where the window adaptor 106 itself acts as a the coupling member, an additional fastener such as a nut may be used in conjunction with the threads 108 on the rod/inserter 104 to tighten the two side blocks 112, 114 of the window adapter 110 against the plate 100. In these implementations, the two side blocks 112, 114 may overlap the edges of the window in the plate 100 and may contain grooves substantially equal to the thickness of the plate on each side of each side block that face the plate 100 to allow the center piece 120 to rest against the face of the graft through the window in the plate 100 while accommodating for the thickness of the plate 100. In implementations where window adapters 110 are used, the distance along the end of the rod/inserter 104 that contains threads 108 may be extended to accommodate the full distance from the center hole of the graft to the outer edge of the adapter. Two thread sizes and/or rotations may be employed to allow the rod 104 to tighten into the graft 78 and allow the window adaptor 110 or coupling member 106 to tighten down over the rod 104.

In implementations of cervical spinal surgical systems disclosed herein that involve securing the plate directly to the graft, the positioning of the plate along the midline may be controlled due to the self-centering behavior of the graft. However, because the plate may be able to rotate slightly around the rod during the process of drilling the pilot screw holes, the orthogonality of the plate with the midline may be more difficult to control even though the plate is held against the graft through the coupling member. Various window adaptor designs may allow for better cleaning and sterilization capability due to the ability of the side blocks and the center piece to be fully separated from each other.

Figure 14:
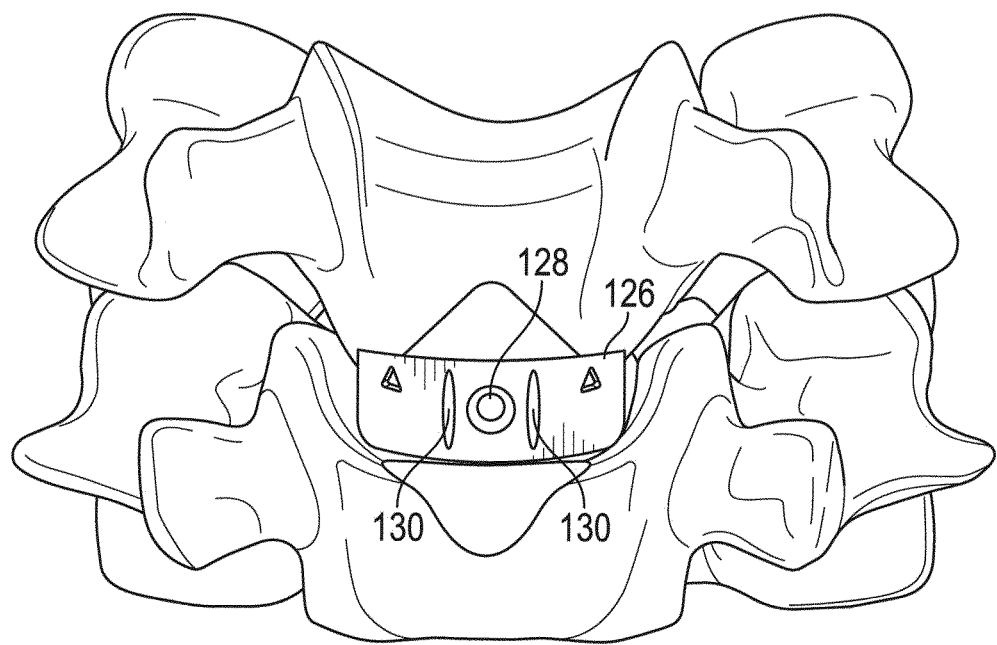
FIG. 14 is a front view of a first implementation of a graft inserted between two vertebrae.
Figure 15A:
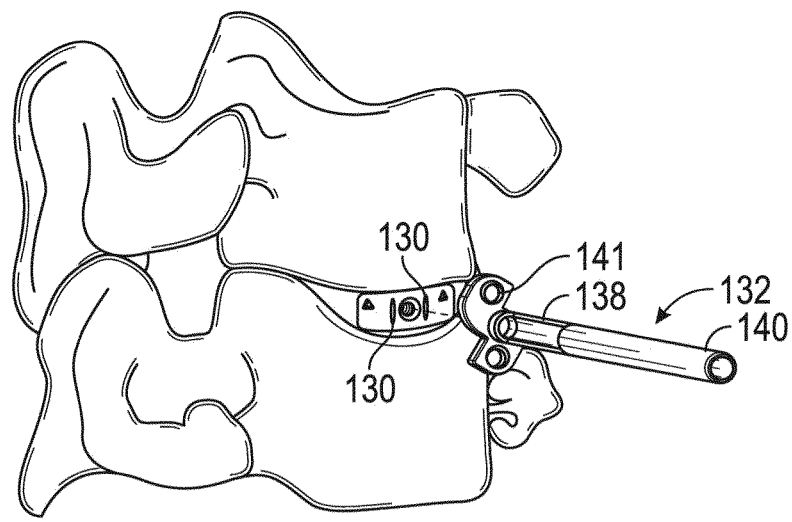
FIG. 15A is an exploded perspective view of an implementation of an eighth implementation of a template adjacent to a graft implementation like that illustrated in FIG. 14.
Figure 15B:
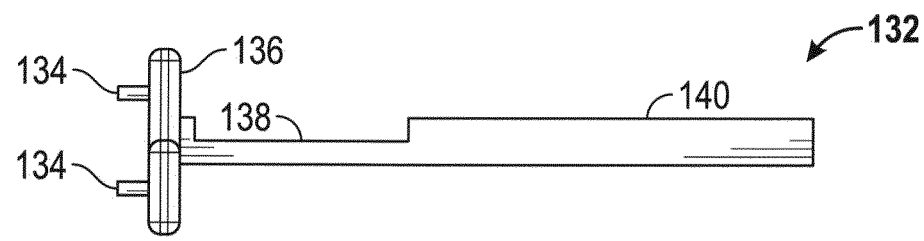
FIG. 15B is a top view of the eighth template implementation illustrated in FIG. 15A.
Figure 16A:
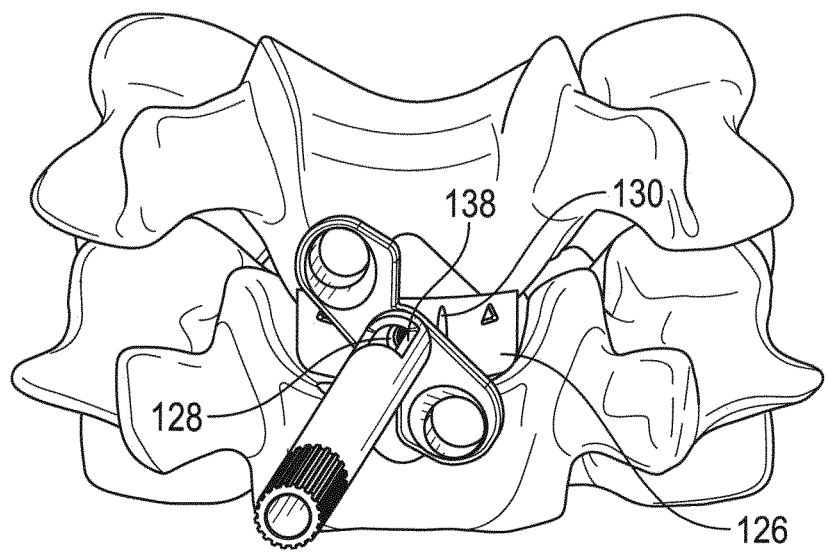
FIG. 16A is a perspective view of the eighth template implementation adjacent to the graft implementation illustrated in FIG. 14.
Figure 16B:
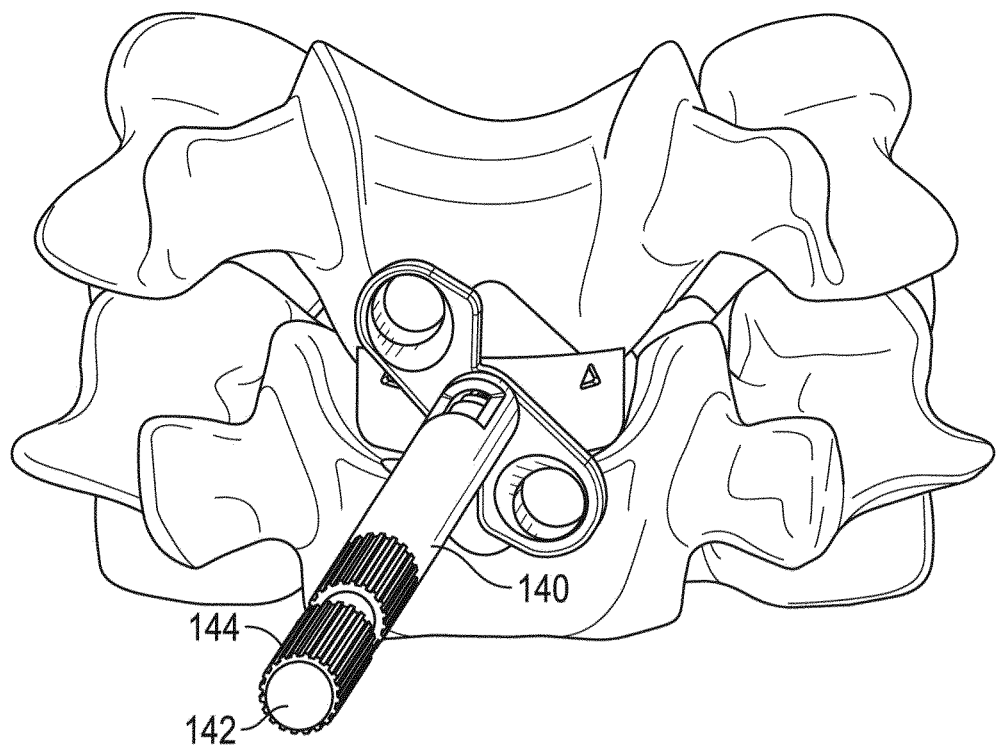
FIG. 16B is a perspective view of an inserter inserted into a sleeve of the eighth template implementation and inserted into the graft.
Figure 16C:
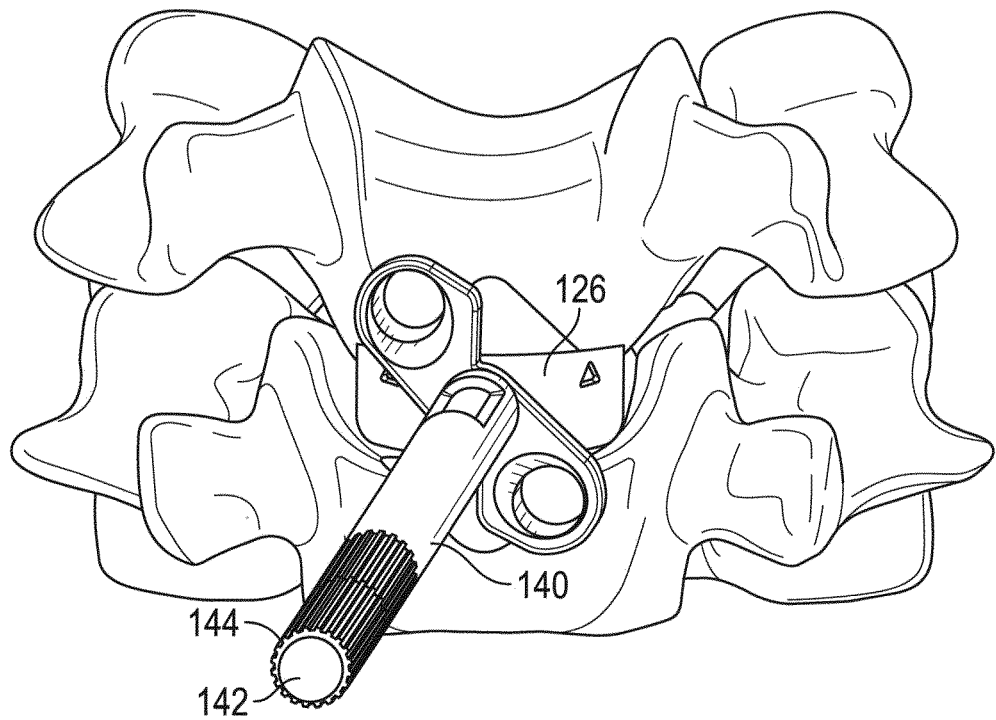
FIG. 16C is a perspective view of the inserter fully coupled with the graft and securing the template to the graft through a flange on the inserter.

Referring to FIG. 14, an implementation of a graft 126 is illustrated inserted between two vertebrae, which have had the rostral and caudal areas immediately next to the graft flattened to aid in attaching the plate. As illustrated, the graft includes center hole 128 and two template openings 130 in the graft. Referring to FIGS. 15A and 15B, the template openings 130 are configured to allow two prongs 134 to couple into them where the two prongs 134 extend from an end 136 of an eighth implementation of a template 132. As illustrated, the template 132 includes a view opening 138 in a sleeve 140 attached to the end 136, which contains one or more pilot screw holes 141 therethrough (which are located on winged portions on the end 136). View opening 138 is a portion of the sleeve 140 that is not present or has been removed to permit the surgeon to see what has been inserted into the sleeve 140. During use, the template 132 may be coupled to the graft 126 through the template openings 130 and the two prongs 134. As can be observed in FIG. 16A, the view opening 138 permits the surgeon to see the center hole 128 of the graft 126. Referring to FIG. 16B, an inserter 142 with an end containing a flange 144 sized to engage with an end of the sleeve 140 (or rod different from the inserter that originally inserted the graft 126 into position) is inserted into the sleeve 140 and engaged with the center hole 128. Referring to FIG. 16C, As the inserter 142 is screwed into the center hole 128 of the graft 126, the flange 144 engages with and presses the sleeve 140 and the end 136 of the template 132 against the graft 126. Once the inserter 142 has been fully screwed into the graft 126, the template 132 is held against the graft 126. The two prongs 134 are resting in the template openings 130 and work to prevent any rotation of the template 132 while the pilot screw holes 141 are being used during the pilot screw hole drilling process.

The same principles disclosed above in the discussion of FIGS. 14-16C may be employed for trials where the trial handle is capable of being removed and reinserted after placement of the trial. In these implementations, an identical template design to that illustrated in the above figures may be used and an identically designed trial handle with a flange may be employed to secure the template in an identical manner to the trial. In these implementations, the pilot screw holes would be aligned diagonally as in the implementation illustrated in FIGS. 14-16C.

Figure 24:
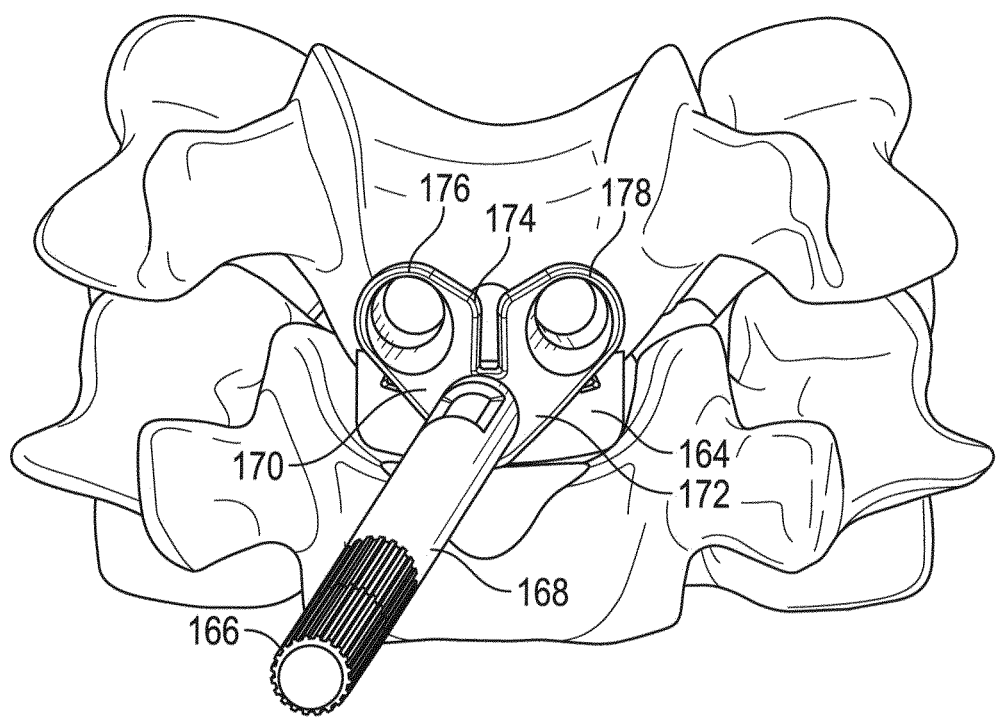
FIG. 24 is a front view of another implementation of a template.

Other implementations are possible as well that involve trials that have removable and reinsertable handles. FIG. 24 illustrates an implementation of a template 168 that can be employed with a trial 164 that has a removable handle 166. In this implementations, the template 168 is configured to be held against the trial 164 through the flange on the end of the removable handle 166. In this implementation, the template 168 includes two winged portions 170, 172 at the end of the template 168 and prongs similar to the design illustrated in FIG. 15B. The two winged portions 170, 172 are located on either side of the midline location in a mirrored configuration over the same vertebra which create an opening 174 between them that can allow the surgeon to see the mark tattooed to the surface of the vertebra over the midline. This opening can be used by the surgeon to double check the midline position of the template and the trial 164 as the surgery is proceeding. Once the template 168 has been secured to the trial 164 after the removable handle 166 has been inserted through the sleeved template and the flange of the handle 166 has been tightened against the sleeve, the surgeon can then drill pilot screw holes using the pilot screw holes 176, 178 located through the two winged portions 170, 172 of the template 168. Implementations like those illustrated in FIG. 24 may be useful when doing multi-level spinal fusions, as they allow the surgeon to use the template 168 to establish the midline position of the plate to be set on either the uppermost or lowest vertebra by drilling just two holes initially In various implementations, the use of the two holes may simultaneously secure both the midline position and ensure orthogonality of the plate based on the principles disclosed in this document.

Several implementations of various interbody grafts and trials have been disclosed in this document. Additional implementations of grafts and trials disclosed in the following section may also be used with any of the cervical spinal surgical systems disclosed herein.

Figure 17:
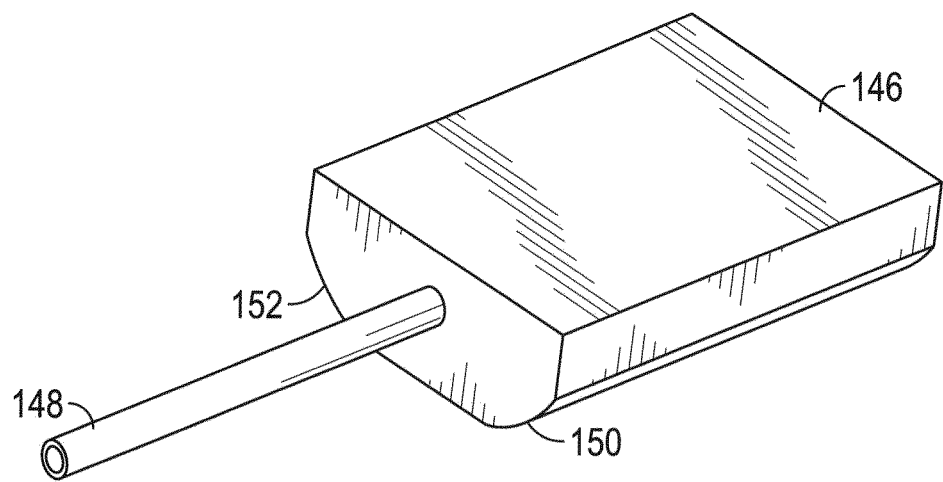
FIG. 17 is a perspective view of an implementation of a trial.

The average distance from the uncal vertebral joint on one side of a vertebra to the uncal vertebral joint on the other side ranges from about 15 mm to about 16 mm at C4-5 to about 17 mm to about 18 mm at C5-6 and C6-7. The total distance from joint to joint ranges from about 17 mm to about 18 mm at C4-5 to about 20 mm to about 21 mm at C5-6 and C6-7. A subtle flattening of the uncal joint slope also exists as one proceeds caudally in the subaxial spine. Because these measurements are remarkably constant when compared between men and women of different heights, implementations of trials and interbody grafts that correspond to these measurements and incorporate slopes on two edges that correlate with the slope of the uncal joints of a specific cervical vertebra pair may be constructed. The measurements and an example of a trial 146 comprising a handle 148 that includes two opposing edges 150, 152 that incorporate a slope that correlate with or correspond with the slope of the uncal vertebral joint is illustrated in FIG. 17.

Interbody grafts of all types may also be modified to incorporate similarly sloped opposing edges that correlate with or correspond to the slope of the uncal vertebral joint. Because of the presence of the sloped opposing edges, the graft may be enabled to be more self-centering than before (and similarly, a trial with similarly sloped opposing edges will exhibit similar self-aligning behavior). In particular implementations, grafts that are PEEK interbody devices like those disclosed herein may be modified in a similar fashion to incorporate these rounded structures. An example of such an implementation of a graft 154 is illustrated in FIG. 18.

Figure 18:
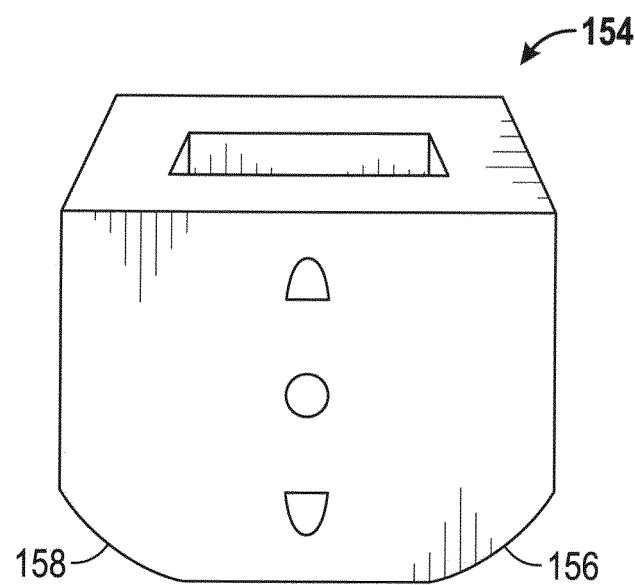
FIG. 18 is a front perspective view of an implementation of a graft.

In the implementation illustrated in FIG. 18, the rounding of the two opposing edges 156, 158 may occur about 2 mm from each side of the graft. The distance between the two opposing edges 156, 158 where the rounding begins is about 12 mm in this implementation. Because the proportions of the uncal vertebral joints and the spacing between them is consistent across both men and women, the measurements described for the graft 154 illustrated in FIG. 18 may work for the vast majority of patients. However, other graft sizes for specific situations may also be selected to accommodate specific cases. The principles disclosed in this document may also be used to perform similar modifications to cortical cancellous grafts.

Use of the modified graft implementations disclosed herein may also allow for optimization of the bone-graft interface by permitting a larger portion of the surface of the graft facing the vertebrae to contact the vertebral surfaces. Because the two opposing edges 156, 158 of the graft 154 are sloped, the graft 154 is capable of achieving closer proximity to a vertebral surface caudal to it that is rounded than if the graft 154 had sharp square edges which hold the graft 154 away from the vertebral surface beneath it. The presence of a gap between the surfaces of the graft and the vertebral surface poses a challenge to the fusion process and creates risk that the fusion will not take place as successfully and/or that recovery time will be prolonged.

As has been discussed, cervical spinal surgical systems like those disclosed herein may be utilized to ensure that the alignment of the plate is orthogonal and aligned with the midline of the vertebrae involved in a fusion surgery as well as ensuring that a plate that is not longer than necessary is used to make the fusion possible. Conventional surgical techniques present midline alignment issues caused by movement of the plate caused during drilling of the pilot screw holes. When the plate has moved from being directly over the midline, a longer plate is likely to be required. Also, as was previously mentioned, due to the presence of the uncal vertebral joints, the grafts naturally tend to self-center, as do the trials during surgery. Because interbody grafts do not have a coronal tilt, aligning the plate using the trial which corresponds with the ultimate alignment of the interbody graft may geometrically ensure an orthogonal plate.

Figure 19:
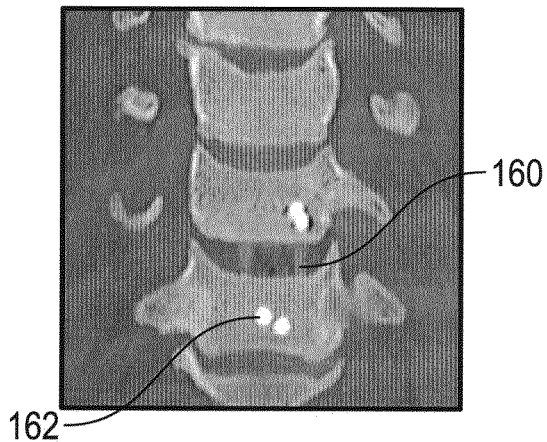
FIG. 19 is an CT scan of a plate screwed to two vertebrae illustrating the position of a graft.

That this tendency for the graft to self-center exists even when the plate is not orthogonal can be seen in FIG. 19 (a CT reconstruction) where the graft 160 is lying within the relative center of the uncal joint while the white dots 162 indicate the position of the screws of the plate, which can be seen is tilted to the right significantly.

Figure 20:
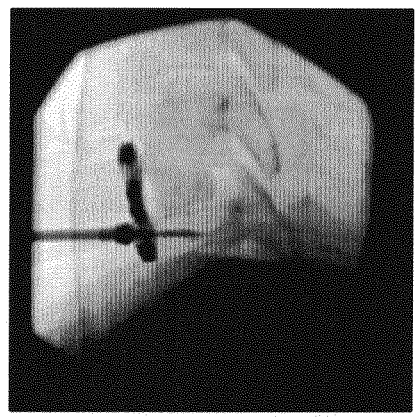
FIG. 20 is a lateral intraoperative fluoroscopic image of a plate showing a first plate holding pin.
Figure 21:
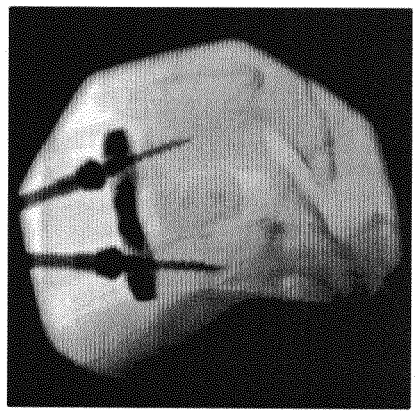
FIG. 21 is a lateral intraoperative fluoroscopic image of a plate showing a first and second plate holding pin.
Figure 22:
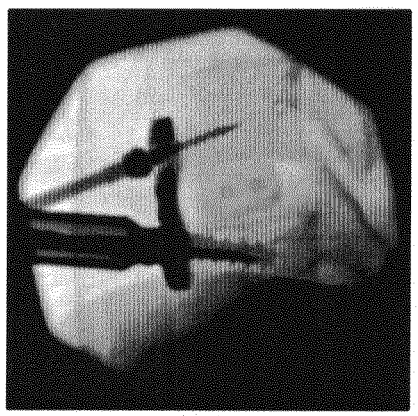
FIG. 22 is a lateral intraoperative fluoroscopic image of a plate showing a plate screw.
Figure 23:
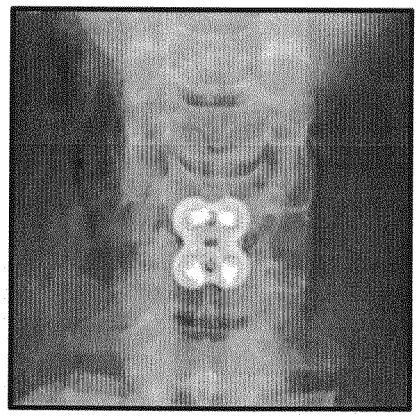
FIG. 23 is a post operative AP x-ray image indicating the midline positioning of the plate on the cervical vertebrae.

FIGS. 20-22 illustrate sequential lateral intraoperative fluoroscopic images of a plate placed after the midline was previously visually identified and plate holding pins pre-drilled. FIG. 20 illustrates the first plate holding pin screwed in place and FIG. 21 illustrates the second plate holding pin screwed in place. A fixed angle drill guide was then used to drill holes into the vertebral bodies with the plate immobilized by the plate holding pins. A plate screw inserted into the caudal vertebral body can be seen in the image of FIG. 22. FIG. 23 is a post-operative AP x-ray indicating midline placement of the cervical plate without the use of any AP fluoroscopic imaging during surgery to control the need to identify the midline position of the plate under plate limiting visualization conditions once the plate was placed over the graft. These images demonstrate proof of the concept that the use of predrilled holes following identification of the midline and plate holding pins can maintain the plate in midline position through the process of drilling of the pilot screw holes and can result in midline placement of the plate.

Implementations of templates, plates, inserters, grafts, and other implementing components may be made of any of a wide variety of conventional and other materials, including by non-limiting example, metals, plastics, composites, biologics, ceramics, and the like.

In places where the description above refers to particular implementations of cervical spinal surgical systems, it should be readily apparent that a number of modifications may be made without departing from the spirit thereof and that these implementations may be applied to other cervical spinal surgical systems.

What is claimed is:

1. A device for use in a cervical spinal operation comprising:
   a trial comprising:
      two sloped surfaces, each of the two sloped surfaces corresponding with a sloped surface of a concave portion of an uncal vertebral joint of a cervical vertebra when the trial is inserted between two cervical vertebrae;
      a first flat surface configured to face the concave portion of an uncal vertebral joint of a cervical vertebra when the trial is inserted between two cervical vertebra; and
      a second flat surface opposing the first flat surface;
   wherein an area of the second flat surface is greater than an area of the first flat surface.

2. The device of claim 1, wherein the trial is configured to automatically center a handle over a midline position of two vertebrae through the two sloped surfaces.

3. The device of claim 1, wherein the trial is configured to fit between one of a C4 and C5 vertebrae, the C5 and C6 vertebrae, or the C6 and C7 vertebrae.

4. The device of claim 1, further comprising a handle configured to removably couple to the trial.

5. A device for use in a cervical spinal operation comprising:
   a trial comprising a handle removably coupled to the trial, the trial comprising;
      a flat first surface parallel with a length of the handle; and
      a second surface opposing the flat first surface, the second surface comprising:
         a flat first portion; and
         a second portion and a third portion each comprising a sloped surface extending from the flat first portion of the second surface towards the first surface;
   wherein a width of the flat first surface is greater than a width of the flat first portion of the second surface; and
   wherein the width of the flat first surface and the width of the flat first portion of the second surface are measured perpendicular to the length of the handle.

6. The device of claim 5, wherein the sloped surface of the second portion and the sloped surface of the third portion correspond with a slope of a concave portion of an uncal vertebral joint of a cervical vertebra when the trial is inserted between two cervical vertebrae.

7. The device of claim 5, wherein the trial is configured to automatically center the handle over a midline position of two vertebrae through the second portion and the third portion.

8. The device of claim 5, wherein the handle is configured to screw into the trial.

9. The device of claim 5, wherein the second portion and the third portion are symmetrical about the handle.

10. The device of claim 5, wherein the trial is configured to fit between one of a C4 and C5 vertebrae, the C5 and C6 vertebrae, or the C6 and C7 vertebrae.

11. A trial for use in a cervical spinal operation comprising:
   a block comprising a first end, a second end opposite the first end, a first face, and a second face opposite the first face; and
   a handle removably coupled to the first end of the block;
   wherein the first face comprises a first flat surface configured to face a portion of an uncal vertebral joint opposite a concave portion of the uncal vertebral joint when the trial is inserted between two cervical vertebrae;
   wherein the second face comprises a sloped surface and a second flat surface;
   wherein the sloped surface corresponds with a slope of a concave portion of an uncal vertebral joint of a cervical vertebra when the trial is inserted between two cervical vertebra;
   wherein a perimeter of the first flat surface is greater than a perimeter of the second flat surface.

12. The trial of claim 11, wherein the trial is configured to automatically center the handle over a midline position of two vertebrae through the second face.

13. The trial of claim 11, wherein the handle is configured to screw into the first end of the block.

14. The trial of claim 11, wherein an outer perimeter of the second end is substantially a hexagon.

15. The trial of claim 11, wherein substantially 4 mm of a width of the second face is sloped, wherein the width is measured perpendicular to a longest length of the handle.

16. The trial of claim 11, wherein the trial is configured to fit between one of a C4 and C5 vertebrae, the C5 and C6 vertebrae, or the C6 and C7 vertebrae.

* * * * *